US00PP14792P3

(12) United States Plant Patent
Zipperer, III

(10) Patent No.: US PP14,792 P3
(45) Date of Patent: May 18, 2004

(54) GLADIOLUS PLANT NAMED 'MAGIC LAVENDER'

(50) Latin Name: *Gladiolus×grandiflora*
Varietal Denomination: Magic Lavender

(76) Inventor: John O. Zipperer, III, 13590 Brynwood La., Ft. Myers, FL (US) 33912

( * ) Notice: Subject to any disclaimer, the term of this patent is extended or adjusted under 35 U.S.C. 154(b) by 0 days.

(21) Appl. No.: 10/173,136

(22) Filed: Jun. 17, 2002

(65) Prior Publication Data

US 2003/0233693 P1 Dec. 18, 2003

(51) Int. Cl.[7] ..... A01H 5/00
(52) U.S. Cl. ..... Plt./301
(58) Field of Search ..... Plt./301

(56) References Cited

PUBLICATIONS

U.S. patent application Ser. No. 09/745,086, Zipperer, III, filed Dec. 20, 2000.
U.S. patent application Ser. No. 09/742,726, Zipperer, III, filed Dec. 20, 2000.
U.S. patent application Ser. No. 09/877,571, Zipperer, III, filed Jun. 8, 2001.
U.S. patent application Ser. No. 09/877,572, Zipperer, III, filed Jun. 8, 2001.
U.S. patent application Ser. No. 09/877,573, Zipperer, III, filed Jun. 8, 2001.
U.S. patent application Ser. No. 09/877,574, Zipperer, III, filed Jun. 8, 2001.
U.S. patent application Ser. No. 09/877,575, Zipperer, III, filed Jun. 8, 2001.
U.S. patent application Ser. No. 09/918,662, Zipperer, III, filed Jul. 31, 2001.
U.S. patent application Ser. No. 09/918,660, Zipperer, III, filed Jul. 31, 2001.
U.S. patent application Ser. No. 09/918,663, Zipperer, III, filed Jul. 31, 2001.

*Primary Examiner*—Bruce R. Campell
*Assistant Examiner*—Michelle Kizilkaya
(74) *Attorney, Agent, or Firm*—Hahn Loeser & Parks LLP; Laura G. Barrow

(57) ABSTRACT

A new and distinct gladiolus variety, designated 'Magic Lavender', is shown and described. Compared to the 'T-704' variety, the 'Magic Lavender' variety produces spikes that are 8 cm taller and a head length that is 3 cm longer. The bloom of the variety comprises three large purple colored petals, two medium-sized purple colored petals, and one small white petal having a splash of purple fanning up the center of the petal.

2 Drawing Sheets

Botanical classification: *Gladiolus×grandiflora*.
Varietal denomination: 'Magic Lavender'.

The present invention comprises a new and distinct cultivar of a Gladiolus plant referred to by the variety name 'Magic Lavender'.

ASEXUAL REPRODUCTION

The new variety of gladiolus was originated by the Applicant in a controlled proprietary breeding program in Ft. Myers, Fla. wherein selected gladiolus varieties were crossed. The female parent was an unpatented lavender colored gladiolus variety named 'T-704', having a spike length near 115 cm from a Jumbo size bulb, a long head having about 18–20 florets, and a medium-weighted stem. The male parent was an unpatented purple-colored gladiolus variety named 'Spartan', having a spike length of about 115 cm from a Jumbo size bulb, floppy wide foliage, a heavy stem, and about 16–18 florets per stem. The seeds were planted in Ft. Myers, Fla. Asexual reproduction of the 'Magic Lavender' cultivar was achieved in Ft. Myers, Fla. by collecting, and subsequently growing to maturity, cormels from the first corm. All subsequent asexual reproductions of the 'Magic Lavender' are true to the original variety.

BOTANICAL DESCRIPTION

Figure 1:
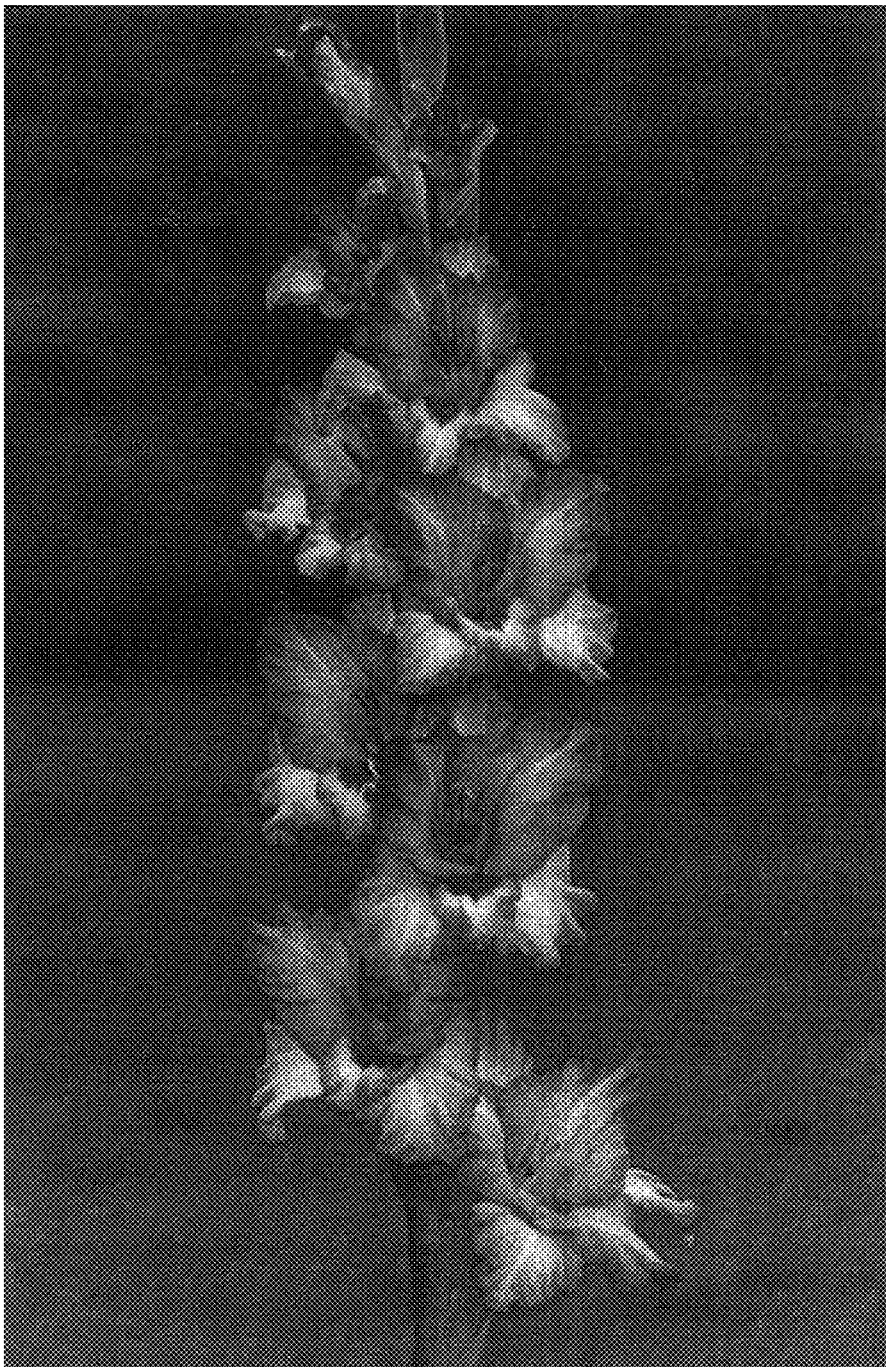
FIG. 1 is a photograph of the 'Magic Lavender' variety in bloom.

The accompanying color photograph (FIG. 1) shows the inflorescence and various stages of blooming of a 'Magic Lavender' variety.

The following botanical description of the 'Magic Lavender' variety was observed when the plant was 77 days old grown in Ecuador under the following conditions.

1) Twelve-hour daylight days with high light intensity;
2) Temperatures: 60° F. (low's) and 76° F. (high's);
3) Humidity: 60%.
4) Rainfall: 2–3 inches/month.

All color descriptions with respect to parts of the variety, where color is a distinguishing feature, are made to The Royal Horticultural Society Colour Chart (R.H.S.), except where terms of ordinary usage and dictionary meaning are used. Color observations with respect to The R.H.S. Colour Chart were made in the Netherlands under similar environmental conditions as described above, but at increased day lengths of 12 to 17 hours and 50% to 65% humidity.

Figure 2:
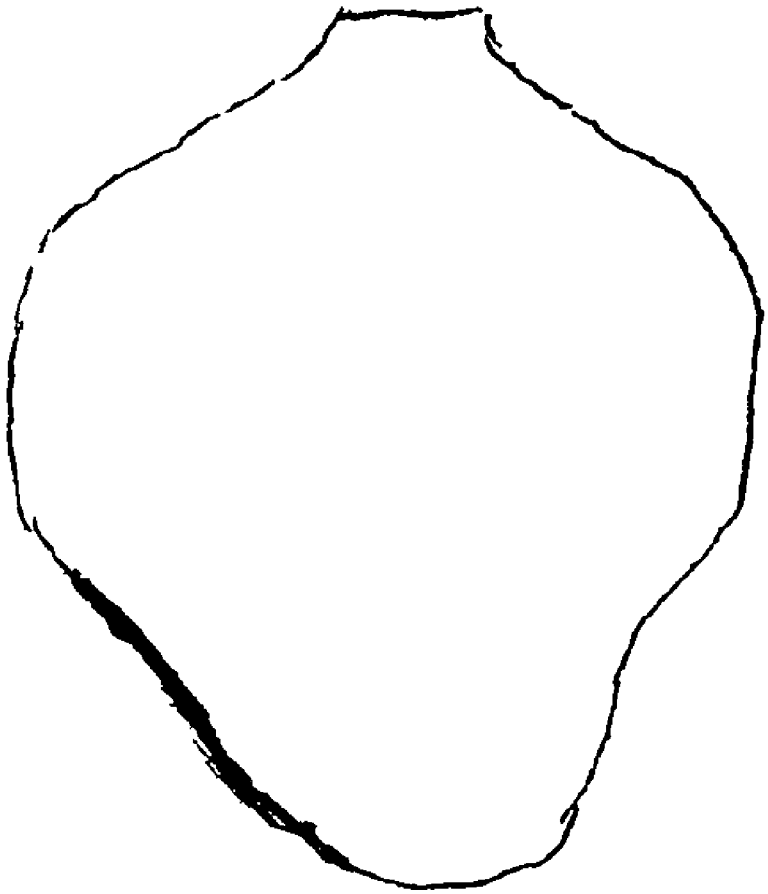
FIG. 2 is a drawing illustrating the shape of the large petals.

The bud size of the 'Magic Lavender' cultivar, when first showing color, is 6 cm in length. The flowers of the 'Magic Lavender' cultivar each comprise three large petals, two medium-size petals, and one small petal at the lower part of the corolla. All of the petals of the corolla are present in an overlapping arrangement. The shape of the large petals is illustrated best in FIG. 2, with dimensions of 2–2.25 inches in length and 1.75 inches in width (at the widest point, then tapering down as shown).

The color of the tight bud is purple violet (group N80C). The color of the flower going down deep in the throat is red-purple group N74A. The flower in perfect condition is made up of three large petals, each having a purple color (group 76C), with purple- violet colored edges (group N80B). The two medium-size petals have a purple color (group 77D), with purple colored edges (group N78B). The single small petal is white (group 155D) (with a splash of purple (group N78B) that fans up the center of the petal. The edges of the small petal are purple colored (group 77C).

The corolla bloom, in declining condition, is purple (group 76D) with purple edges (group N78C) on the three large petals. The two medium size petals are purple (group 77D) with purple edges (group 78B). The single small petal is white (group 155C) with the splash of purple described above remaining the same shade (i.e. group N78A), with the edges of the small petal also remaining the same shade of purple (i.e. group 77C).

The variety has three stamens and one pistil. The color of tbe pistil head is purple group 76D. The color of the pistil stem is white group 155D. The color of the stamen head is Purple Group 79B on one side and white group 155A on the backside of the head. The color of the top part of the stamen stem is red-purple group N74B.

The stem between the buds on the flower head is yellow green (group 144B). The leaves are Green group 137C. Various factors will affect spike length, however, including temperature (larger spikes occur in cooler weather), irrigation, light intensity, fertilization, soil type (larger spikes occur in heavy soils versus sandy soil), and bulb size (larger bulbs result in larger spikes).

The corms of the 'Magic Lavender' variety are typical for the gladiolus and have a red-purple color (group 63D) under the husk on the top of the bulb one day after harvest.

This variety can produce stems 120 cm long from a #2 bulb. The variety will typically have 18 florets, a head length of 48 cm, and a bloom diameter of 10 cm. The foliage stands up fairly erect, with a leaf length of 72 cm and a leaf width of 3.5 cm.

GENERAL OBSERVATIONS

Compared to the gladiolus variety 'T-704', the 'Magic Lavender' variety produces spikes that are 8 cm taller and a head length that is 3 cm taller. The 'Magic Lavender' variety is also much more resistant to foliar diseases than the 'T-704' variety.

The 'Magic Lavender' cultivar does not emit a fragrance.

The flowers of the 'Magic Lavender' variety will bloom under long and short day lengths and opens rapidly enough to be cut with only one flower showing color. The cut stems of the variety can also be shipped for up to one week prior to blooming and still open well thereafter.

Compared to its parent 'Spartan', the 'Magic Lavender' variety produces spikes which are 8 cm taller and which contain two to four more blooms. The 'Magic Lavender' variety is more resistant to Fusarium species than the 'Spartan' variety, but is similar to 'Spartan' in its ability to produce heavy stems. Both 'Spartan' and 'Magic Lavender' are more resistant to infection by Curvalaria and Botyris species than the 'T-704' variety.

The 'Magic Lavender' variety is most similar to the parent 'Spartan' variety (i.e. the most similar variety to 'Magic Lavender') in terms of its resistance to Curvalaria and Botyris species and its ability to produce heavy stems.

I claim:

1. A new and distinct gladiolus plant, cultivar 'Magic Lavender', as shown and described herein.

* * * * *